US009796667B2

(12) United States Patent
Green et al.

(10) Patent No.: US 9,796,667 B2
(45) Date of Patent: *Oct. 24, 2017

(54) NITRONE COMPOUNDS AND THEIR USE IN PERSONAL CARE

(71) Applicant: Dow Global Technologies LLC, Midland, MI (US)

(72) Inventors: George David Green, Cary, IL (US); Raymond J. Swedo, Mount Prospect, IL (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/461,956

(22) Filed: Mar. 17, 2017

(65) Prior Publication Data
US 2017/0190655 A1 Jul. 6, 2017

Related U.S. Application Data

(63) Continuation of application No. 15/310,513, filed as application No. PCT/US2015/029655 on May 7, 2015, now Pat. No. 9,730,874.

(Continued)

(51) Int. Cl.
C07C 251/30 (2006.01)
A61K 8/41 (2006.01)
(Continued)

(52) U.S. Cl.
CPC ............ C07C 251/30 (2013.01); A61K 8/416 (2013.01); A61Q 19/00 (2013.01); A61Q 19/08 (2013.01)

(58) Field of Classification Search
None
See application file for complete search history.

(56) References Cited

U.S. PATENT DOCUMENTS 5,176,983 A 1/1993 Horn et al.
5,273,863 A 12/1993 Horn et al.
(Continued)

FOREIGN PATENT DOCUMENTS

CN 102153498 A 8/2011
DE 10201223 A1 7/2003
(Continued)

OTHER PUBLICATIONS

Antioxidant Activity Applying an Improved ABTS Radical Cation Decolorization Assay, N.Re et al, Free Radical Biology & Medicine, vol. 26, Issues 9-10, pp. 1231-1237, 1997.

Wang et al; Evaluation of Resveratrol Derivatives As Potential Antioxidants and Identification of a Reaction Product of Resveratrol and 2,2-Diphenyl-1-Picryhydrazyl Radical; J. Agric. Food Chem, vol. 47, pp. 3974-3977, 1999.
Fang et al; Structure-Activity Relationship and Mechanism of the Tocopherol-Regenerating Activity of Resveratrol and Its Analogues; J. Agric. Food Chem.; vol. 56, pp. 11458-11463, 2008.
Fabris, et al; Antioxidant Properties of Resveratrol and Piceid on Lipid Peroxidation in Micelles and Monolamellar Liposomes; Biophysical Chemistry, vol. 135, pp. 76-83, 2008.
Hung, et al; Delivery of Resveratrol, A Red Wine Polyphenol, From Solutions and Hydrogels Via the Skin; Biol. Phar. Bull, vol. 31, pp. 955-962, 2008.
Lee, et al; Resveratrol With Antioxidant Activiy Inhibits Matrix Metalloproteinase Via Modulation of SIRT1 in Human Fibrosarcoma Cells; Life Sciences, vol. 88, pp. 465-472, 2011.
Kasiotis, et al; Resveratrol and Related Stilbenes: Their Anti-Aging and Anti-Angiogenic Properties; Food and Chemical Toxicology, vol. 61, pp. 112-12-, 2013.
Croitoru, M D. "Nitrones Are Able to Release Nitric Oxide in Aqueous Environment Under Hydroxyl Free Radical Attack", Nitric Oxide: Biology and Chemistry, vol. 25, No. 3, pp. 309-3015, 2011.

(Continued)

Primary Examiner — Karl J Puttlitz
(74) Attorney, Agent, or Firm — Edward L. Brant

(57) ABSTRACT

Provided are compounds and compositions thereof that are useful as antioxidants in personal care formulations. The compounds are of the Formula I:

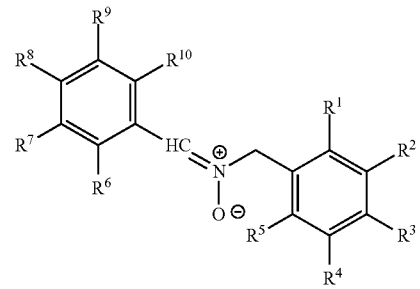

wherein $R^1$, $R^2$, $R^3$, $R^4$, and $R^5$ are independently H, —OH, $C_1$-$C_6$ alkoxy, —COOH, —COO$^-$M$^+$ or —O$^{31}$ M$^+$, where M$^+$ is a sodium, potassium, or ammonium ion, wherein at least two of $R^1$, $R^2$, $R^3$, $R^4$, or $R^5$ are —OH, and $R^6$, $R^7$, $R^8$, $R^9$, and $R^{10}$, are independently H, —OH, $C_1$-$C_6$ alkoxy, —COOH, —COO$^-$M$^+$ or —O$^-$M$^+$ where M$^+$ is a sodium, potassium, or ammonium ion, or a substituent of Formula II:

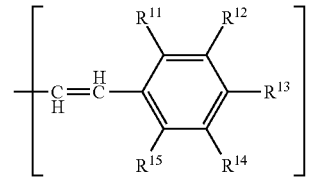

wherein $R^{11}$, $R^{12}$, $R^{13}$, $R^{14}$, and $R^{15}$ are independently H, —OH, $C_1$-$C_6$ alkoxy, —COOH, —COO$^-$M$^+$ or —O$^-$M$^+$, where M$^+$ is a sodium, potassium, or ammonium ion, provided that one of $R^6$, $R^7$, $R^8$, $R^9$, and $R^{10}$ is a substituent of Formula II.

8 Claims, No Drawings

Related U.S. Application Data

(60) Provisional application No. 61/991,796, filed on May 12, 2014.

(51) Int. Cl.
*A61Q 19/00* (2006.01)
*A61Q 19/08* (2006.01)

(56) References Cited

U.S. PATENT DOCUMENTS

| | | | |
|---|---|---|---|
| 5,455,272 | A | 10/1995 | Janzen et al. |
| 6,002,001 | A | 12/1999 | Carney et al. |
| 7,655,251 | B2 | 2/2010 | Durand et al. |
| 2004/0241261 | A1 | 12/2004 | Prous et al. |
| 2012/0058088 | A1 | 3/2012 | Sardi |
| 2014/0303255 | A1 | 10/2014 | Dhamdhere et al. |

FOREIGN PATENT DOCUMENTS

| | | |
|---|---|---|
| EP | 1591104 A1 | 11/2005 |
| ES | 2316312 A1 | 4/2009 |
| IN | 1377CHE2009 | 8/2012 |
| JP | 2011251914 A | 12/2011 |
| WO | 9222290 A1 | 12/1992 |
| WO | 02065993 A2 | 8/2002 |
| WO | 2005041905 A2 | 5/2005 |
| WO | 2009108999 A1 | 9/2009 |
| WO | 2011130400 A1 | 10/2011 |
| WO | 2012150370 A1 | 11/2012 |
| WO | 2013081778 A2 | 6/2013 |

OTHER PUBLICATIONS

Scott, G. "Mechanisms of Antioxidant Action: Rubber Bound Antioxidants Based on Nitrones-1, Non-Sulphur Vulcanizates", European Polymer Journal, vol. 14, pp. 905-912, Pergamon Press LTD 1978.

Samadi, A. "Synthesis, Structure, Theoretical and Experimental Invitro Antioxidant/Pharmacological Properties of X-Aryl, N-Alkyl Nitrones As Potential Agents for the Treatment of Cerebral Ischemia", Bioorganic & Medicinal Chemistry 19 pp. 951-960, 2011.

Floyd, R. "Nitrones, Their Value As Therapeutics and Probes to Understand Aging", Mechanisms of Aging and Development 123, pp. 1021-1031, 2002.

Hensley, K. "Nitrone-Based Free Radical Traps As Neuroprotective Agents in Cerebral Ischaemia and Other Pathologies", IRN 40, Chapter 13, pp. 299-317, Academic Press Limited, 1997.

Bagheri, R. "Mechanisms of Antioxidant Action: Evidence for a Regenerative Cycle During the Melt Stabilisation of Polypropylene by Galvinoxyl", Polymer Degradation and Stability, vol. 5, pp. 145-160, 1983.

Zou, et al; Fabrication of Surface-Modified CDSE Quantum Dots by Self-Assembly of a Functionalizable Comb Polymer, Polymer International, vol. 5, Issue 60, pp. 751-757, 2011.

Hill, R.; Spin Traps: The New Anti-Oxidant?; Beautymagonline (Retrieved Mar. 29, 2013), Retrieved From the Internet, <URL:http://www.beautymagonline.com/beauty-articles-4/1112-spin-traps-2>, pp. 1-3.

Perricone, N.; The Wrinkle Cure: The Formula for Stopping Time, Vintage/Ebury (A Division of Random); Illustrated Edition, pp. 182-186, Jul. 1, 2001.

Kliegel et al; Canadian Journal of Chemistry, vol. 76, Issue 7, pp. 1082-1092, 1998.

Burgess, C.; Cosmetic Dermatology, p. 19, 2005.

NITRONE COMPOUNDS AND THEIR USE IN PERSONAL CARE

FIELD OF THE INVENTION

This invention relates generally to compounds and compositions that are useful as antioxidants in personal care formulations. The compounds contain both nitrone and phenolic functionalities.

BACKGROUND

Personal care compositions are important products for most consumers. Personal care compositions contain a variety of additives that provide a wide array of benefits to the composition.

Antioxidants are among the additives commonly used in personal care compositions. Antioxidants help protect the skin from the damaging effects of free radicals caused by various environmental stresses, such as exposure to UV rays. Free radicals include, for example, singlet oxygen. Free radicals cause damage to the skin with the end result being a loss of elasticity of the skin and the appearance of wrinkles leading to premature aging of the skin.

Based on the physiological mechanism of the aging process, oxidative stress due to increased level of reactive oxygen species (ROS) especially caused by physiological stress or solar ultraviolet radiation can accelerate skin aging. There is evidence that intrinsic and extrinsic aging (i.e., photoaging) have several overlapping biochemical and molecular mechanisms. Type I collagen constitutes the major structural component of dermal connective tissue and provides dermis with tensile strength and stability. Degradation of collagen in the dermis has been reported in intrinsic aged and photoaged skin. Additionally, a major signaling pathway contributing to photoaging by ROS is the up-regulation of matrix metalloproteinase-1 (MMP-1), which leads to degradation of dermal collagen, associated with aging spots and wrinkles. Therefore, stronger antioxidants are needed as potential anti-aging ingredients to provide protection.

One such antioxidant that has been studied, as disclosed in WO 2012/150370, is resveratrol (3,5,4'-trihydroxy-trans-stilbene). Resveratrol is a naturally occurring polyphenolic compound found in the skin of grapes and other fruits. It has been investigated in the context of its potential chemopreventive properties against skin damage from UV exposure and against ROS induced damage associated with brain function, heart disease, and cancer. However, the natural abundance of resveratrol is low, and it is thus very expensive.

Consequently, there is a need to develop new antioxidant compositions for use in personal care, including compositions that mitigate degradation of collagen in skin.

STATEMENT OF INVENTION

We have now found that nitrones with pendant stilbene groups have equivalent efficacy as radical scavengers at lower concentrations (as measured by duration of antioxidant protection), or higher efficacy (less oxidative damage and/or longer antioxidant protection) at equivalent concentrations as compared to conventional antioxidants. It has also been found that the performance of nitrones cannot be achieved by simply adding two different antioxidants, e.g., one with a phenolic functionality and another with nitrone functionality. Rather, the presence of both functionalities in the same molecule is an important aspect of their favorable performance.

Accordingly, one aspect of the invention provides a compound of Formula I:

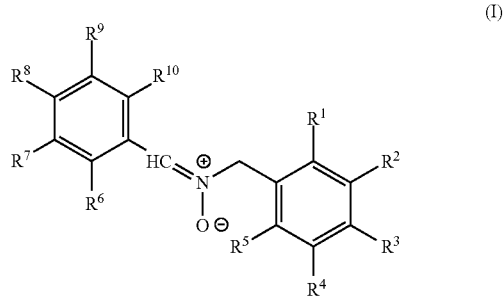

(I)

wherein $R^1$, $R^2$, $R^3$, $R^4$, and $R^5$ are independently H, —OH, $C_1$-$C_6$ alkoxy, —COOH, —COO$^-$M$^+$ or —O$^{31}$ M$^+$, where M$^+$ is a sodium, potassium, or ammonium ion, and $R^6$, $R^7$, $R^8$, $R^9$, and $R^{10}$, are independently H, —OH, $C_1$-$C_6$ alkoxy, —COOH, —COO$^-$M$^+$ or —O$^-$M$^+$, where M$^+$ is a sodium, potassium, or ammonium ion, or a substituent of Formula II:

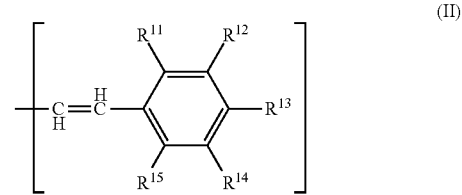

(II)

wherein $R_{11}$, $R_{12}$, $R_{13}$, $R_{14}$, and $R_{15}$ are independently H, —OH, $C_1$-$C_6$ alkoxy, —COOH, —COO$^-$M$^+$ or —O$^-$M$^+$, where M$^+$ is a sodium, potassium, or ammonium ion, provided that one of $R^6$, $R^7$, $R^8$, $R^9$, and $R^{10}$ is a substituent of Formula II.

Another aspect of the invention provides a personal care composition comprising (a) an antioxidant compound of Formula I, and (b) a dermatologically acceptable carrier.

In another aspect, the invention provides a cosmetic method of treating skin which comprises applying to the skin a composition as described herein.

In a still further aspect, there is provided a method for inhibiting the degradation of collagen, the method comprising topically administering to skin an effective amount of a composition as described herein.

In a yet further aspect, there is provided a method for reducing the visible signs of aging, the method comprising applying to skin in need of such treatment a composition as described herein.

DETAILED DESCRIPTION

Unless otherwise indicated, numeric ranges, for instance as in "from 2 to 10," are inclusive of the numbers defining the range (e.g., 2 and 10).

Unless otherwise indicated, ratios, percentages, parts, and the like are by weight. "Room temperature," as used in this specification, is the ambient temperature, for example, 20-25° C.

"Alkyl," as used in this specification, encompasses straight and branched chain aliphatic hydrocarbon groups having the indicated number of carbon atoms. If no number is indicated, then 1-6 alkyl carbons are contemplated. Unless otherwise indicated, the alkyl group is optionally substituted with 1, 2, or 3, preferably 1 or 2, more preferably 1, substituents that are compatible with the syntheses described herein. Such substituents include, but are not limited to, nitro, halogen, carboxylic acids (e.g., $C_0$-$C_6$-COOH), $C_2$-$C_6$ alkene, cyano, amido, and/or ester. Unless otherwise indicated, the foregoing substituent groups are not themselves further substituted.

As noted above, in one aspect the invention provides a compound of Formula I. In another aspect, the invention provides a composition comprising a compound of Formula I and a dermatologically acceptable carrier.

In some embodiments, at least one of $R^1$, $R^2$, $R^3$, $R^4$, or $R^5$ in the compounds of Formula I is —OH. In some embodiments, at least two of $R^1$, $R^2$, $R^3$, $R^4$, or $R^5$ in the compounds of Formula I are —OH.

In some embodiments, at least one of $R^6$, $R^7$, $R^8$, $R^9$, or $R^{10}$ is —OH. In some embodiments, at least one of $R^6$ or $R^{10}$ is —OH.

In some embodiments, at least one of $R_{11}$, $R_{12}$, $R_{13}$, $R_{14}$, or $R^{15}$ is —OH. In some embodiments, $R^{13}$ is —OH.

In some embodiments, at least one of $R_{11}$, $R_{12}$, $R_{13}$, $R_{14}$, or $R_{15}$ is $C_1$-$C_6$ alkoxy. In some embodiments, $R^{12}$ or $R^{14}$ is methoxy.

In some embodiments of the composition of the invention, the compound of Formula I is as shown in Table 1:

TABLE 1

Specified Compounds of Formula I

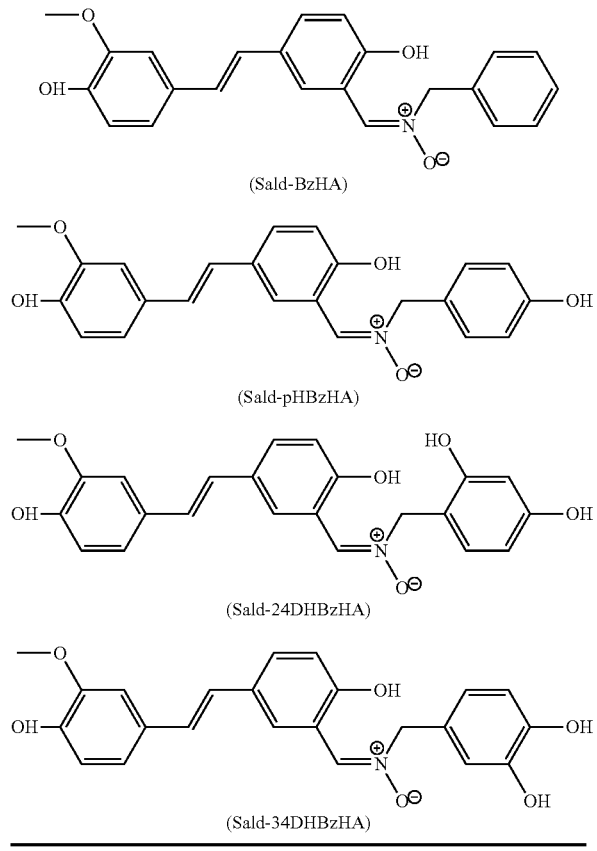

(Sald-BzHA)

(Sald-pHBzHA)

(Sald-24DHBzHA)

(Sald-34DHBzHA)

A person of ordinary skill in the art can readily determine the effective amount of the antioxidant compound of Formula I that should be used in a particular composition in order to provide the benefits described herein (e.g., free radical scavenging and inhibition of collagen degradation), via a combination of general knowledge of the applicable field as well as routine experimentation where needed. By way of non-limiting example, the amount of the compound of Formula I in the composition of the invention may be in the range of from 0.01 to 5 weight percent, preferably from 0.05 to 3 weight percent, and more preferably from 0.1 to 1 weight percent, based on the total weight of the composition.

Compounds of Formula I may be readily prepared by those skilled in the art using known synthetic techniques. For instance, the compounds may be prepared by the reaction of a stilbene aldehyde compound (possibly containing one or more hydroxyl groups, such as (E)-2-hydroxy-5-(4-hydroxy-3-methoxystyryl)benzaldehyde) with a benzylhydroxylamine compound (also possibly containing one or more hydroxyl groups on the phenyl, such as 3,4-dihydroxybenzylhydroxylamine), followed by isolation and purification of the desired product.

Compositions of the invention also include a dermatologically acceptable carrier. Such material is typically characterized as a carrier or a diluent that does not cause significant irritation to the skin and does not negate the activity and properties of active agent(s) in the composition. Examples of dermatologically acceptable carriers that are useful in the invention include, without limitation, emulsions, creams, aqueous solutions, oils, ointments, pastes, gels, lotions, milks, foams, suspensions, powders, or mixtures thereof. In some embodiments, the composition contains from about 99.99 to about 50 percent by weight of the dermatologically acceptable carrier, based on the total weight of the composition.

The dermatologically acceptable carrier of the invention may also include, for instance, water, a thickener, an emollient, an emulsifier, a humectant, a surfactant, a suspending agent, a film forming agent, a foam building agent, a preservative, an antifoaming agent, a fragrance, a lower monoalcoholic polyol, a high boiling point solvent, a propellant, a colorant, a pigment, glycerin, a mineral oil, silicon feel modifiers, preservatives, emollients, or mixtures thereof.

Other additives may be included in the compositions of the invention such as, but not limited to, abrasives, absorbents, aesthetic components such as fragrances, pigments, colorings/colorants, essential oils, skin sensates, astringents (e.g., clove oil, menthol, camphor, eucalyptus oil, eugenol, menthyl lactate, witch hazel distillate), anti-caking agents, antifoaming agents, antimicrobial agents (e.g., iodopropyl butylcarbamate), other antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin bleaching and lightening agents (e.g., hydroquinone, kojic acid, ascorbic acid, magnesium ascorbyl phosphate, ascorbyl glucosamine), skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, thickeners, and vitamins (e.g., Vitamin C) and derivatives thereof.

The composition of the invention may be, for example, in the form of an oil, a gel, a solid stick, a lotion, a cream, a milk, an aerosol, a spray, a foam, a mousse, an ointment or a fatty ointment or a powder.

Compositions of the invention may be used in a variety of personal care applications, such as in cosmetics and in skin care (e.g., lotions, creams, oils, topical medicines, and sunscreens).

The compositions of the invention may be manufactured by processes well known in the art, e.g., by means of conventional mixing, dissolving, granulating, emulsifying, encapsulating, entrapping or lyophilizing processes.

As noted above, compositions of the invention, containing a compound of Formula I, are highly effective as radical scavengers. They exhibit significantly better antioxidant attributes compared to previously known antioxidants for personal care applications. Furthermore it has been found that the performance of nitrones that have phenolic groups cannot be achieved by simply adding two different antioxidants, one with a phenolic functionality and another with nitrone functionality. Rather, the presence of both functionalities in the same molecule is an important aspect of their favorable performance.

The cosmetic compositions of the invention are useful for the treatment and protection of skin from free radicals caused, for instance, by exposure to ultraviolet light, such as UVA and UVB rays, as well as other harmful forms of radiation, such as long wave infrared.

Thus, for instance, the cosmetic compositions may be used in a method for inhibiting the degradation of collagen. According to such method, an effective amount of the composition may be topically administering to skin in need of such treatment.

The compositions may also be used in a method for reducing the visible signs of aging, which may result from the radical induced degradation of collagen in the skin, by applying to skin in need of such treatment the composition. Visible signs of aging may include, for instance, development of textural discontinuities such as wrinkles and coarse deep wrinkles, skin lines, crevices, bumps, large pores, or unevenness or roughness, reducing fine lines, loss of skin elasticity (loss and/or inactivation of functional skin elastin), sagging (including puffiness in the eye area and jowls), loss of skin firmness, loss of skin tightness, loss of skin recoil from deformation, discoloration (including undereye circles), blotching, sallowness, hyperpigmented skin regions such as age spots and freckles, keratoses, abnormal differentiation, hyperkeratinization, elastosis, and other histological changes in the stratum corneum, dermis, epidermis, the skin vascular system (e.g., telangiectasia or spider vessels), and underlying tissues, especially those proximate to the skin.

In practicing the methods of the invention, the cosmetic composition are generally administered topically by applying or spreading the compositions onto the skin. A person of ordinary skill in the art can readily determine the frequency with which the cosmetic compositions should be applied. The frequency may depend, for example, on the amount of sunlight that an individual is likely to encounter in a given day and/or the sensitivity of the individual to sunlight. By way of non-limiting example, administration on a frequency of at least once per day may be desirable.

Some embodiments of the invention will now be described in detail in the following Examples.

EXAMPLES

Example 1

Synthesis of the Oxime Precursor
3,4-Dihydroxybenzaldehyde Oxime (34DHBzOx)

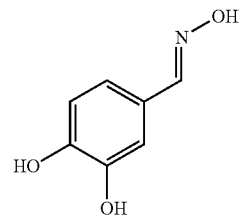 [SMILES: O/N=C/c1ccc(O)c(O)c1]

A 100 mL 3-neck flask was equipped with a magnetic stirrer, a reflux condenser, an addition funnel, a thermocouple, an ice bath, and a nitrogen blanket. The flask was charged with 13.81 grams (0.10 mole) of 3,4-dihydroxybenzaldehyde and with 50 mL of 100% ethanol. The mixture was stirred at room temperature under nitrogen to give a clear dark brown solution. The solution was cooled to <15° C. The addition funnel was charged with 6.63 grams (0.10 mole) of 50 wt. % aqueous hydroxylamine solution. The hydroxylamine solution was added to the cooled aldehyde solution over a period of about 45 minutes. During the addition, the reaction mixture temperature was maintained at <20° C. After completing the hydroxylamine solution addition, the reaction mixture was heated at 55° C. until GC analysis showed that the aldehyde was essentially gone (about 7 hours). The reaction mixture was solvent-stripped by rotary evaporation to give a quantitative yield of the oxime as a brown solid. Structure was confirmed by IR, NMR, and GC/MS analyses.

IR analyses were performed using a Nicolet 560 FTIR spectrometer. For liquid samples, a small drop was cast as a neat film between two KBr plates. For solid samples, KBr dispersions were pressed. The IR spectrum was acquired in the transmission mode from 4000 to 400 cm$^{-1}$, with a spectral resolution of 4 cm$^{-1}$. A Happ-Genzel type apodization function was used.

Both $^1$H and $^{13}$C NMR spectra were acquired using a Bruker 200 NMR spectrometer operating at 4.7 T. $^1$H spectra were obtained using an 8.2 second accumulation time and 2.0 KHz sweep width; the $^{13}$C spectra were obtained at a 4.7 second accumulation time and 7.0 KHz sweep width. Methanol-d4 was typically used as the solvent. Chemical shifts were referenced using the solvent resonances at 3.30 ppm for $^1$H, and at 59.05 ppm for $^{13}$C.

GC/MS analyses were performed using a Hewlett Packard Model 6890 GC system with an Agilent Mass Selective Detector operating in electron ionization (EI) mode and in positive chemical ionization (CI) mode. The carrier gas for the EI mode was helium at approximately 1 mL/minute. Methane was used as the carrier gas for the CI mode. The column was a J&W Scientific DB-5MS, 30 meter×0.25 mm×1µm film. The initial oven temperature was 60° C. with a hold time of 5 minutes. The temperature was ramped at 10° C./minute to 220° C. with a hold of 2 minutes, and then it was ramped at 20° C./minute to 290° C. The injector temperature was 225° C. The sample size was 1 μL for EI mode, and 1 μL for CI mode. The split ratio was 50:1.

Example 2

Synthesis of the Hydroxylamine Precursor 4-((Hydroxyamino)methyl)benzene-1,2-diol (34DHBzHA)

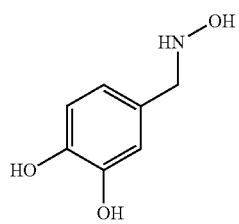 [SMILES: ONCc1ccc(O)c(O)c1]

A 125 mL 3-neck flask was equipped with a magnetic stirrer, a sintered glass sparging tube, a pH electrode with meter, and a Claisen adapter fitted with a thermocouple and a gas outlet. The flask was charged with 4.59 grams (0.03 mole) of the 3,4-dihydroxybenzaldehyde oxime (34DHBzOx) prepared in Example 1 above and with 40 mL of methanol. The mixture was stirred at room temperature to give a clear brown solution. Sodium cyanoborohydride (1.89 grams, 0.03 mole) was then added to the oxime solution in one portion. A lecture bottle of hydrogen chloride gas was connected to the sparging tube with a safety trap in between. The HCl bottle was opened just enough to allow a trickle of gas to sparge into the reaction mixture. The pH of the mixture dropped quickly from about 7 to <3. At the same time, the reaction mixture foamed vigorously and solids began to precipitate. Sparging with HCl was stopped, and the pH was monitored. After the pH had stabilized at ≤3 for 1 hour, the reaction mixture was filtered and the white solids were washed on the filter with small portions of methanol. After drying, 1.38 grams of white solid were obtained. The filtrate and methanol washings were combined, and the solvent was removed by rotary evaporation to give 6.27 grams of beige solids. These solids were combined with the solids obtained by filtration, and were dissolved in about 25 mL of water to give a clear brown solution having pH about 5. The pH was increased to about 8 by the addition of a saturated aqueous solution of sodium bicarbonate. At this point, solids began to separate out. The mixture was cooled in an ice bath for about 1 hour, then it was filtered. The solids were washed on the filter with portions of water. After drying under vacuum at 55° C. for about 1 hour, the yield of hydroxylamine as a dark brown solid was 2.56 grams (55% yield). The structure was confirmed by IR and NMR analyses using the procedures described in Example 1 above.

Example 3

Synthesis of Stilbene Aldehyde Precursor (E)-2-hydroxy-5-(4-hydroxy-3-methoxystyryl) benzaldehyde (Sald)

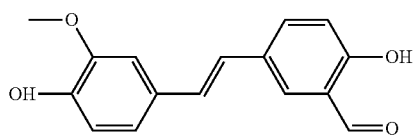 [SMILES: COc1cc(/C=C/c2ccc(O)c(C=O)c2)ccc1O]

A flask was charged with 25 g (0.166 moles) of 2-methoxy-4-vinylphenol in 300 mL of anhydrous DMF. The following compounds were added to the resulting solution in order under stirring and nitrogen purge: 34.94 g (0.166 mole) of 3,5-bromosalicyaldehyde, 0.745 g (0.0033 mole) of palladium acetate, 0.201 g (0.0006 mole) of tri-o-tolylphosphine, and 34.64 mL (0.249 moles, 1.5 equivalent) of triethylamine. The mixture was heated for 30 hours at 110° C. and filtered through a Celite 545 packed funnel at room temperature. The composition was extracted with 50 mL of chloroform, followed by washing with 100 mL of water three times. The organic layer was dried over $MgSO_4$. After removing the solvent under vacuum, the stilbene aldehyde compound was isolated by column chromatography on silica gel (chloroform). The resulting oil was crystallized by 5 mL of ethyl acetate and 100 mL of hexane at 2° C. The yield of purified product obtained was 16.23 g (36.4%). The structure was confirmed by $^1$H-NMR, $^{13}$C-NMR, and MS analyses using the procedures described in Example 1 above.

Example 4

Synthesis of the Stilbene-Pendant Nitrone N-(2-Hydroxy-5-(4-hydroxy-3-methoxystyryl)benzylidene)-1-phenylmethanamine oxide (Sald-BzHA)

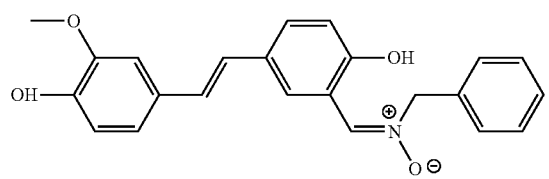 [SMILES: COc1cc(/C=C/c2ccc(O)c(/C=[N+](/[O-])Cc3ccccc3)c2)ccc1O]

A 25 mL 1-neck flask was equipped with a magnetic stirrer and a reflux condenser. The flask was charged with 0.2705 grams (0.001 mole) of the stilbene aldehyde (Sald) precursor prepared in Example 3 above, with 7 mL of toluene and 7 mL of methanol. The mixture was stirred and warmed to 50° C. until a clear amber solution was obtained. The hydroxylamine precursor benzylhydroxylamine hydrochloride in an amount of 0.1599 grams (0.001 mole) and 0.0590 grams (0.00056 mole) of anhydrous sodium carbonate were added to a separate small flask along with 2 mL of water. The generation of gas was observed, and a white suspension was formed. This suspension was added to the aldehyde solution in one portion. A yellow solid began to form immediately. The mixture was held at 50° C. for 4 hours. The resulting mixture was a yellow paste. A small amount (about 5 mL) of water was added to the mixture, and then the mixture was filtered. The yellow solids were washed on the filter with small portions of water. The solids were dried in a vacuum oven at 55° C. for a few hours to give 0.241 grams of yellow solid stilbene-pendant nitrone product. Yield=64.3%. The structure was confirmed by IR, $^1$H- and $^{13}$C-NMR analyses using the procedures described in Example 1 above.

Example 5

Synthesis of the Stilbene-Pendant Nitrone N-(2-Hydroxy-5-(4-hydroxy-3-methoxystyryl)benzylidene)-1-hydroxyphenylmethanamine oxide (Sald-pHBzHA)

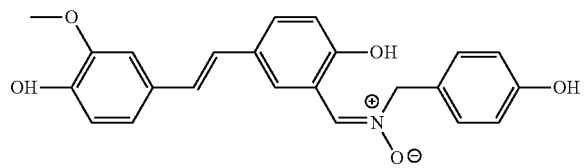 [SMILES: COc1cc(/C=C/c2ccc(O)c(/C=[N+](/[O-])Cc3ccc(O)cc3)c2)ccc1O]

A 25 mL 1-neck flask was equipped with a magnetic stirrer and a reflux condenser. The flask was charged with 0.2694 grams (0.001 mole) of the stilbene aldehyde (Sald) precursor prepared in Example 3 above, with 7 mL of toluene and 7 mL of methanol. The mixture was stirred and warmed to 50° C. until a clear amber solution was obtained. The hydroxylamine precursor p-hydroxybenzylhydroxyamine (pHBzHA) in an amount of 0.1391 grams (0.001 mole) was added to the aldehyde solution in one portion. The mixture was held at 50° C. for 4.5 hours. The reaction mixture was cooled to room temperature; a yellow solid separated from solution. The mixture was cooled in a refrigerator for several hours, then the cold mixture was filtered. The solids were washed on the filter with a small amount of methanol. The product was dried in a vacuum oven at 45° C. for about 4 hours to give 0.157 grams of the stilbene-pendant nitrone product. Yield=40.1%. The structure was confirmed by IR, $^1$H- and $^{13}$C-NMR analyses using the procedures described in Example 1 above.

Example 6

Synthesis of the Stilbene-Pendant Nitrone N-(2-Hydroxy-5-(4-hydroxy-3-methoxystyryl)benzylidene)-1-(2,4-dihydroxyphenyl)methanamine oxide (Sald-24DHBzHA)

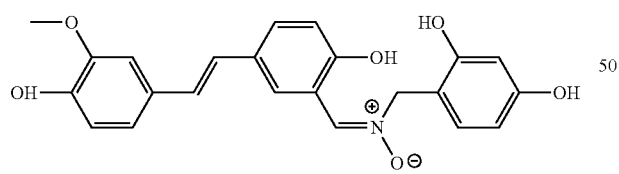

A 25 mL 1-neck flask was equipped with a magnetic stirrer and a reflux condenser. The flask was charged with 0.2708 grams (0.001 mole) of the stilbene aldehyde (Sald) precursor prepared in Example 3 above, with 7 mL of toluene and 7 mL of methanol. The mixture was stirred and was warmed to 50° C. until a clear amber solution was obtained. The hydroxylamine precursor 2,4-dihydroxybenzylhydroxylamine (24DHBzHA) in an amount of 0.1551 grams (0.001 mole) was added in one portion. The mixture was held at 50° C. for 4.5 hours. No solids formed upon cooling the mixture to room temperature. The solvents were removed by rotary evaporation to give a brown-yellow solid. This residue was dried in a vacuum oven at 55° C. for about 4 hours to give 0.3825 grams of the stilbene-pendant nitrone product. Yield=94%. The structure was confirmed by IR, $^1$H- and $^{13}$C-NMR analyses using the procedures described in Example 1 above.

Example 7

Synthesis of the Stilbene-Pendant Nitrone N-(2-Hydroxy-5-(4-hydroxy-3-methoxystyryl)benzylidene)-1-(3,4-dihydroxyphenyl)methanamine oxide (Sald-34DHBzHA)

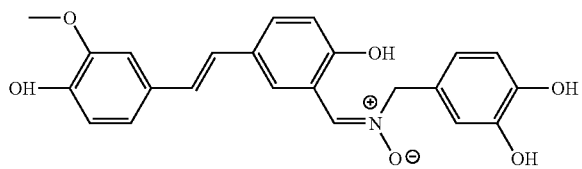 [SMILES: COc1cc(/C=C/c2ccc(O)c(/C=[N+](/[O-])Cc3ccc(O)c(O)c3)c2)ccc1O]

A 25 mL 1-neck flask was equipped with a magnetic stirrer and a reflux condenser. The flask was charged with 0.2701 grams (0.001 mole) of the stilbene aldehyde (Sald) prepared in Example 3 above, with 7 mL of toluene and 7 mL of methanol. The mixture was stirred and was warmed to 50° C. until a clear amber solution was obtained. The hydroxylamine precursor 3,4-dihydroxybenzylhydroxylamine (34DHBzHA) in an amount of 0.1547 grams (0.001 mole) was added in one portion. The mixture was held at 50° C. for 4.5 hours. The mixture slurry was cooled to room temperature, and then concentrated by removal of about half of the solvent. The resulting mixture was filtered, and the solids were washed on the filter with small volumes of hexanes. The solids were dried in a vacuum oven at 55° C. for about 3 hours to give 0.2047 grams of the stilbene-pendant nitrone product. Yield=50.3%. The structure was confirmed by IR, $^1$H- and $^{13}$C-NMR analyses using the procedures described in Example 1 above.

Example 8

Characterization of Compounds Synthesized in Examples 1-7

The compounds prepared in Examples 1-7 were characterized for melting point and product purity. Melting points were determined using a Mel-Temp apparatus and are uncorrected. Product purity was determined by GPC analyses (performed using a PerkinElmer Series 200 HPLC) that followed the progress of the synthesis reactions. Two Polymer Laboratories pLgel columns were used in series: (1) 300 nm×7.5 mm, 3μ, 100 Å; and (2) 300 mm×7.5 mm, 5μ, 50 Å. These two columns were preceded by a guard column. The columns were maintained at 35° C. The mobile phase was 100% THF at a flow rate of 2 mL/minute. UV detection was at 270 nm. The program run time was 10 minutes. The melting points and product purity are listed in Table 2.

TABLE 2

Melting Point and Purity of Compounds Synthesized

| Compound | Melting Point (° C.) | % Purity |
|---|---|---|
| 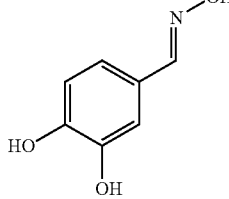 3,4-Dihydroxybenzaldehyde Oxime (34DHBzOx) | 161-163 | >98% |
| 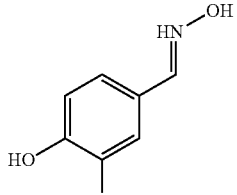 4-((Hydroxyamino)methyl)benzene-1,2-diol (34DHBzHA) | 149-151 | >75 |
| 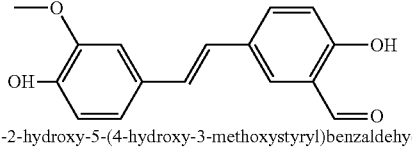 (E)-2-hydroxy-5-(4-hydroxy-3-methoxystyryl)benzaldehyde (Sald) | 172-174 | 97 |
| 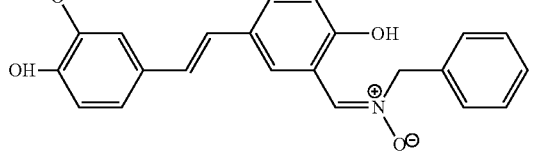 N-(2-Hydroxy-5-(4-hydroxy-3-methoxystyryl)benzylidene)-1-phenylmethanamine oxide (Sald-BzHA) | 204-206 | >95 |
| 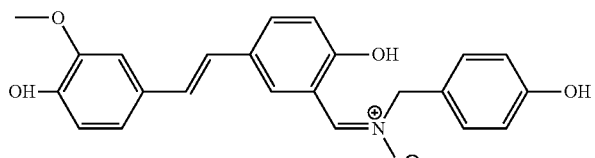 N-(2-Hydroxy-5-(4-hydroxy-3-methoxystyryl)benzylidene)-1-hydroxyphenylmethanamine oxide (Sald-pHBzHA) | 192-197 | >97 |
| 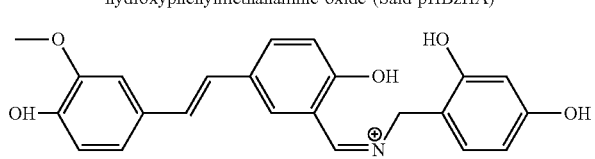 N-(2-Hydroxy-5-(4-hydroxy-3-methoxystyryl)benzylidene)-1-(2,4-dihydroxyphenyl)methanamine oxide (Sald-24DHBzHA) | 136-140 | >91 |
| 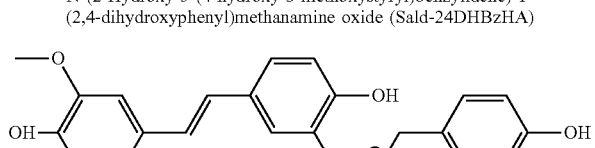 N-(2-Hydroxy-5-(4-hydroxy-3-methoxystyryl)benzylidene)-1-(3,4-dihydroxyphenyl)methanamine oxide (Sald-34DHBzHA) | 193-196 | >91 |

Example 9

Antioxidant Potential

Antioxidant potential is evaluated using the Oxygen Radical Absorbance Capacity (ORAC) protocol. ORAC is a chemical in-vitro method based on the hydrogen atom transfer (HAT) mechanism (see N. Re et al., *Free Radical Biology & Medicine*, 26 (9/10), 1231 (1997)). ORAC measures antioxidant inhibition of peroxyl radical induced oxidations and thus reflects classical radical chain breaking antioxidant activity by H atom transfer. In this assay, the peroxyl radical reacts with a fluorescent probe to form a non-fluorescent product. This is quantitated using a fluorescence measurement. Antioxidant capacity is determined by decreased rate and amount of product formed over time. This assay depends upon the free radical damage to the fluorescent probe resulting in the change in its fluorescence intensity. The change of fluorescence intensity is an indicator of the degree of free radical damage. In the presence of an antioxidant, the inhibition of free radical damage is reflected in higher fluorescence intensity and can be measured as antioxidant capacity against the free radicals. The uniqueness of ORAC assay is that the reaction is driven to completion. This allows calculation of the area under the curve (AUC) and gives an absolute quantitation of antioxidancy as opposed to relative measurements in many other assays.

As noted, the longer it takes to observe a decrease in fluorescence, the higher the antioxidant (AO) potential. From the AUC for a given antioxidant, the AUC for blank is subtracted to give its ORAC value. The concentration of AO needed to give the same AUC values as Trolox is calculated and used to represent the Trolox equivalent AO Capacity (TEAC). Trolox is ((±)-6-Hydroxy-2,5,7,8-tetramethylchromane-2-carboxylic acid, CAS #53188-07-1), and is used as an internal control.

The ORAC test is conducted in the stilbene-pendant nitrone compounds of Table 1 above (inventive compounds) as well as to Vitamin C, Vitamin E, and the following comparative compounds:

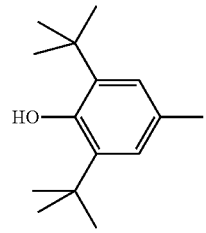

Butylated hydroxytoluene (BHT)

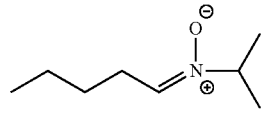

(Z)-N-pentylidenepropan-2-amine oxide (VAL-IPHA)

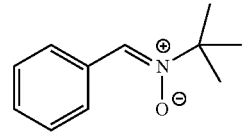

2-Phenyl-N-tert-butylnitrone (PBN)

The inventive stilbene-pendant nitrones in the ORAC test solutions were at a concentration of 100 micromolar, while the concentrations of Trolox, Vitamin C, Vitamin E, BHT, PBN +BHT, and VAL-IPHA were at 100 micromolar. The TEAC values calculated from the ORAC values are listed the Table 3.

TABLE 3

| TEAC Values | |
|---|---|
| ANTIOXIDANT COMPOUND | TEAC |
| Vitamin C (comparative) | 0.76 |
| Vitamin E (comparative) | 0.13 |
| BHT (comparative) | 0.11-0.21 |
| PBN + BHT (comparative) | 0.24 |
| VAL-IPHA (comparative) | 0.18 |

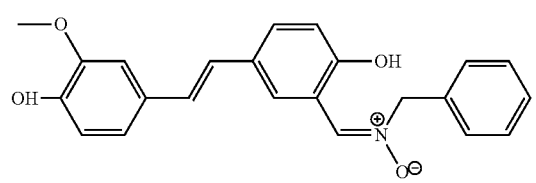 [SMILES: COc1cc(/C=C/c2ccc(O)c(/C=[N+](/[O-])Cc3ccccc3)c2)ccc1O]

Sald-BzHA (inventive) — 8.33

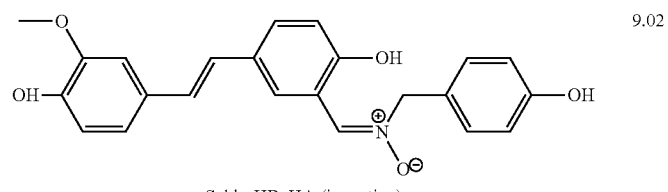

Sald-pHBzHA (inventive) — 9.02

TABLE 3-continued

TEAC Values

| ANTIOXIDANT COMPOUND | TEAC |
|---|---|
| 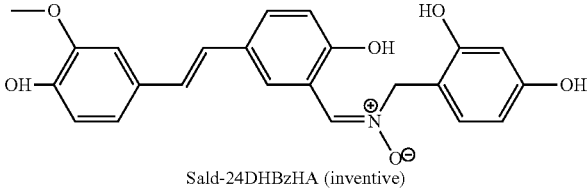 Sald-24DHBzHA (inventive) | 7.31 |
| 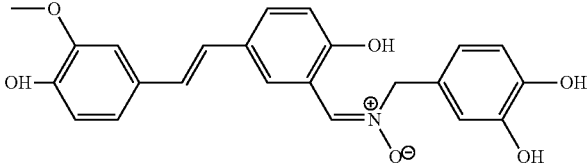 Sald-34-DHBzHA (inventive) | 7.16 |

Surprisingly, it is found that the compounds of the invention displayed significantly higher ORAC values compared to the known antioxidants Vitamin E or C. It is also evident that the TEAC values of phenolic AOs such as BHT, a non-aromatic nitrone such as VAL-IPHA, or an aromatic nitrone such as PBN are not very high compared to the TEAC values of the compounds of the invention. The TEAC value for a physical blend of an aromatic nitrone and a phenolic AO (PBN+BHT) is relatively small also.

What is claimed is:

1. A compound of Formula I:

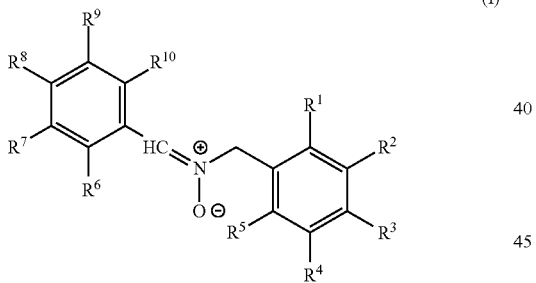

(I)

wherein $R^1$, $R^2$, $R^3$, and $R^4$, and $R_5$ are independently H, —OH, $C_1$—$C_6$ alkoxy, —COOH, —COO$^-$M$^+$ or —O$^-$M$^+$, where M$^+$ is a sodium, potassium, or ammonium ion, and $R^6$, $R^7$, $R^8$, $R^9$, and $R^{10}$, are independently H, —OH, $C_1$—$C_6$ alkoxy, —COOH, —COO$^-$M+ or —O$^-$M$^+$, where M$^+$ is a sodium, potassium, or ammonium ion, or a substituent of Formula II:

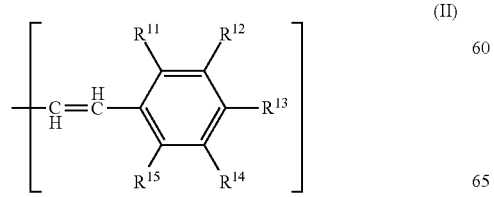

(II)

wherein $R^{11}$, $R^{12}$, $R^{13}$, $R^{14}$, and $R^{15}$ are independently H, —OH, $C_1$—$C_6$ alkoxy, —COOH, —COO$^-$M$^+$ or —O$^-$M$^+$, where M$^+$ is a sodium, potassium, or ammonium ion, provided that one of $R^6$, $R^7$, $R^8$, $R^9$, and $R^{10}$ is a substituent of Formula II, wherein at least two of $R^1$, $R^2$, $R^3$, $R^4$, or $R^5$ are —OH.

2. The compound of claim 1 wherein at least one of $R^6$ or $R^{10}$ is —OH.

3. The compound of claim 1 wherein $R^{13}$ is —OH.

4. The compound of claim 1 wherein $R^{12}$ or $R^{14}$ is methoxy.

5. A personal care composition comprising:

(a) an antioxidant compound of Formula I:

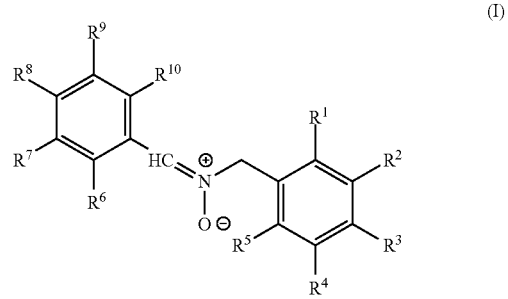

(I)

wherein $R^1$, $R^2$, $R^3$, $R^4$, and $R^5$ are independently H, —OH, $C_1$—$C_6$ alkoxy, —COOH, —COO$^-$M$^+$ or —O$^-$M$^{32}$, where M$^+$ is a sodium, potassium, or ammonium ion, wherein at least two of $R^1$, $R^2$, $R^3$, $R^4$, or $R^5$ are —OH, and $R^6$, $R^7$, $R^8$, $R^9$, and $R^{10}$, are independently H, —OH, $C_1$—$C_6$alkoxy, —COOH, —COO$^-$M$^+$ or —O $^-$M$^+$, where M$^+$ is a sodium, potassium, or ammonium ion, or a substituent of Formula II:

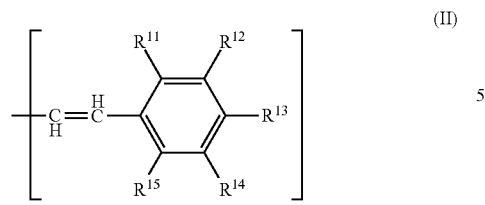

(II)

wherein $R^{11}$, $R^{12}$, $R^{13}$, $R^{14}$, and $R^{15}$ are independently H, —OH, $C_1$—$C_6$ alkoxy, —COOH, —COO$^-$M$^+$ or —O$^-$M$^+$, where M$^+$ is a sodium, potassium, or ammonium ion, provided that one of $R^6$, $R^7$, $R^8$, $R^9$, and $R^{10}$ is a substituent of Formula II; and (b) a dermatologically acceptable carrier.

6. A cosmetic method of treating skin comprising applying to the skin the composition of claim 5.

7. A method for inhibiting the degradation of collagen in skin, the method comprising: topically administering to the skin an effective amount of the composition of claim 5.

8. A method for reducing the visible signs of aging, the method comprising:

applying to skin in need of such treatment the composition of claim 5.

* * * * *